US006357444B1

(12) United States Patent
Parker

(10) Patent No.: US 6,357,444 B1
(45) Date of Patent: Mar. 19, 2002

(54) MOTION LIMITING DEVICE

(76) Inventor: Jonathan A. Parker, 9635 - 29th Ave. N., Plymouth, MN (US) 55441

(*) Notice: Subject to any disclaimer, the term of this patent is extended or adjusted under 35 U.S.C. 154(b) by 0 days.

(21) Appl. No.: 09/025,302

(22) Filed: Feb. 18, 1998

(51) Int. Cl.$^7$ .................................................. A61F 5/56
(52) U.S. Cl. ...................................... 128/848; 602/902
(58) Field of Search .............................. 128/845, 869, 128/871, 873, 874, 848; 2/455, 465, 463, 467, 69, 243.1; 5/633, 632, 630; 602/5, 19, 902

(56) References Cited

U.S. PATENT DOCUMENTS

| 132,500 A | 10/1872 | Sullivan |
| 876,491 A | 1/1908 | Rohwer |
| 898,379 A | 9/1908 | Liebhardt |
| 2,304,235 A | 12/1942 | Boots ............................ 2/114 |
| 3,485,241 A | 12/1969 | Polley ........................ 128/135 |
| 4,507,801 A | * 4/1985 | Kavanagh et al. ............. 2/462 |
| 4,958,644 A | 9/1990 | Rodgers ...................... 128/871 |
| 5,036,865 A | 8/1991 | Keaton ........................ 128/848 |
| 5,122,111 A | * 6/1992 | Sebastian et al. ............. 602/19 |
| 5,201,761 A | * 4/1993 | Serola ..................... 128/845 X |
| 5,216,772 A | 6/1993 | Clute ............................ 5/655 |
| 5,226,193 A | * 7/1993 | Chen ............................ 2/69.5 |
| 5,345,633 A | * 9/1994 | Harnish ........................ 5/639 |
| 5,347,669 A | * 9/1994 | Neviaser et al. ................ 5/655 |
| 5,357,981 A | 10/1994 | Eilam et al. ................. 128/848 |
| 5,383,475 A | 1/1995 | Austin ........................ 128/848 |
| 5,538,015 A | * 7/1996 | Paulson ...................... 128/869 |
| 5,573,014 A | * 11/1996 | Ginter ........................ 128/845 |
| 5,953,749 A | * 9/1999 | Backs ..................... 128/845 X |
| 6,009,873 A | * 1/2000 | Neviaser ..................... 128/845 |

FOREIGN PATENT DOCUMENTS

AT 162244 * 5/1948 ................. 128/871

OTHER PUBLICATIONS

*Flaghouse, Inc.*, Spring 1995, pp. 169,172 and 173.*
*Nordoc Track*, Holiday 1996, p. 22.*

* cited by examiner

Primary Examiner—Denise Pothier
(74) Attorney, Agent, or Firm—Popovich & Wiles, PA

(57) ABSTRACT

An apparatus for limiting body motion as a patient lies down includes a pad shaped to prevent the patient from rolling over the pad. The pad is shaped so that it projects outwardly 3 inches or more from the patient when attached to the human body. The base of the pad contacts the patient's skin or sleep clothes. The pad has sidewalls which make an angle of greater than approximately 35° degrees with respect to the base. A removable, washable covering is placed on the pad. An attachment mechanism associated with the pad and the covering attach the pad and cover to the human body. The attachment mechanism can be a hook-and-loop fastener, a sports bra type device, a series of straps, a series of snaps, or a series of hooks. In each instance, the pad can be positioned at several positions on the body, including positions to the right or left of the patient's medial plane. More than one pad can also be used to limit the body motion of a patient. One can be positioned on the posterior side of a patient and another can be positioned on an anterior side of a patient. In this way, the patient motion may be limited to lying on one side rather than discouraging rest while in the supine position.

4 Claims, 7 Drawing Sheets

MOTION LIMITING DEVICE

FIELD OF THE INVENTION

The present invention relates to the field of devices used to limit the range of motion of a sleeping patient.

BACKGROUND OF THE INVENTION

A good night of sleep is very important to a person's overall health and ability to function in a normal capacity throughout the day. Snoring and obstructive sleep apnea (OSA) are common respiratory obstructive sleep disorders which can significantly affect an individual's quality of sleep as well as the sleep of others. Snoring is very common in the adult population, in that it affects approximately 40% of all adults by the age of 50. Typically, people do not hear themselves snore, but snoring noise can disrupt the sleep of others around them. This can put a strain on family or social relationships and can also be a source of embarrassment for the person who is snoring.

Obstructive sleep apnea ("OSA") is a condition in which there is a complete, or near-complete, obstruction to airflow during sleep. OSA is a significant health problem which is associated with high blood pressure, heart problems and stroke. The most common symptoms associated with OSA are loud snoring and excessive daytime drowsiness. This significant daytime drowsiness can result in difficulty staying awake during meetings or conversation, reading, watching television or, more importantly, while driving. Although the majority of snorers do not have OSA, it is estimated that two-percent of women and four-percent of men in the middle-aged work force have OSA.

The snoring noise is typically produced by vibration of the soft palate and uvula against the back of the throat or the base of the tongue. This usually occurs as a person falls asleep, and these soft tissues, the tongue, and the muscles in the throat area relax. As the tongue relaxes, it will drop back, causing a narrowing of the upper airway. When a person breathes in through a narrower airway, the air moves faster and will cause the tissues to vibrate and the snoring to occur. An apnea event occurs when there is a collapse of the soft tissues in the upper airway which leads to a blockage in airflow of at least ten seconds duration. This cessation in airflow can have a significant physiologic impact on the body, especially the cardiovascular system. The apnea event is usually terminated by a loud snort as the airway re-opens and is associated with a brief awakening, called an arousal, which occurs at the end of the apnea event. These arousals significantly disrupt the sleep of the individual, and can lead to tiredness and fatigue during the day.

It is well known that sleeping in the supine position exacerbates snoring and obstructive sleep apnea. It is common for a bed partner to nudge the snorer with an elbow or foot and instruct the snorer to roll on their side, which will indeed eliminate or greatly reduce the snoring. In addition, research studies have documented that 60% of all patients diagnosed with OSA have a position-dependent OSA. These patients have a dramatic increase in the frequency of apnea events when sleeping in the supine position, versus the side or prone positions. Therefore, sleep position is a significant contributing factor for many patients with sleep-disordered breathing conditions.

The current treatment alternatives for managing snoring and OSA are focused on maintaining the patency of the airway by various means. These treatments include:

Nasal Continuous Positive Airway Pressure (nasal CPAP)—This employs a tight-fitting mask which is attached to a blower that will blow room air under pressure through the nasal passage. This positive airway pressure acts as a pneumatic splint to prevent collapse of the upper airway.

Surgical treatments for management of OSA are designed to correct anatomical abnormalities that lead to airway obstruction, especially in patients with disproportionate anatomy of the nose, maxilla and/or mandible, or the soft tissues of the upper airway. These surgical procedures include nasal reconstruction, uvulopalatopharyngoplasty (UPPP), and various maxillary/mandibular surgical procedures.

Oral appliance therapy involves a treatment program which uses a device worn over the teeth to advance the mandible or tongue in order to increase the size and improve the patency of the airway.

Behavioral therapies are an important part of the overall treatment program for managing snoring and OSA. These adjunctive treatments include managing health and lifestyle conditions such as obesity, alcohol or benzodiazepine consumption, body position, sleep posture, and nasal congestion. These treatments may be used alone or in conjunction with other medical or dental treatment.

The negative impact of sleeping in the supine position is well documented in the research literature; however, treatment of this factor has been largely overlooked by health care providers who are managing snoring and OSA. The current treatments used to prevent patients from sleeping on their backs include use of a tennis ball sewn into the back of the pajamas, placing pillows around body to maintain position, or a gravity-sensitive alarm. Problems with these options make it necessary to consider alternative treatment such as the anti-snoring cushion. The problem with the tennis ball sewn into the pajamas is that the patients are able to roll partially onto their backs and some obese patients are not kept off their backs by the tennis ball. If the individual does roll onto the tennis ball, it will tend to disrupt their sleep by causing them to partially or completely wake. Some patients feel that it is too much of an inconvenience to sew the tennis ball into place. Use of pillows to maintain a certain body position is difficult because the pillows tend to shift or move, during the night, allowing the patient to roll into the supine or unfavorable position. The difficulty with the gravity-sensitive alarm is that it causes the patient to arouse out of deeper sleep or wake completely when the alarm sounds. This leads to disruption of the patient's sleep.

In addition to preventing a patient from sleeping in the supine position to prevent snoring and obstructive sleep apnea, sometimes it is necessary to limit the patient's ability to sleep in certain positions so as to isolate and keep pressure off certain portions of the body. For example, after major surgery, such as a hip or knee joint replacement or shoulder surgery, it is necessary to isolate and keep pressure off that portion of the body to help it to recover properly. Other surgeries also require that a portion of the body be isolated. Unlike preventing one from rolling over into a supine position, with a major surgery it is imperative that the patient isolate these portions of the body for proper recovery. Immediately after surgery of this type, patients are asked to sleep in a partially reclined position, usually in a reclining chair, or a large foam wedge about half of the patient's body length is placed on the bed to prevent the patient from rolling into the surgical site. However, this large foam wedge is uncomfortable to sleep against and it can shift or move during the night. Presently, there is a trend to release patients from the hospital quickly so that the overall cost of health care can be reduced. In order to allow an earlier release, a device is needed which can be used easily at home by a patient to limit the motion during rest or sleep.

There are several problems associated with the pads and systems currently in use. First of all, the shape of the pads does not necessarily prevent a patient from rolling over the pads. Most pads project out from the patient a short distance. These thinner, shorter pads can still allow the patient to roll into a partially supine position in which the torso is at an angle of 20° to 45° to the bed. In this position the head and neck are almost fully supine and the airway can still become fully or partially obstructed. The pads produce discomfort, should a patient roll atop the pad, but they would not prevent one from rolling onto a certain part of the body. Obese patients may not even be affected by the discomfort. In some cases this may be fine for prevention of snoring but in the event of post-surgery treatment the patient must be prevented from rolling onto a shoulder or recently replaced hip or knee.

As a result, there is a need for a method and apparatus for limiting the motion of a patient while at rest or while sleeping. There is a need for a pad which will prevent a patient from reaching the supine or near-supine position to prevent snoring or sleep apnea, as well as to isolate certain areas on the body after surgery. There is also a need for a method and system that can be easily understood and easily used by the patient.

SUMMARY OF THE INVENTION

An apparatus for limiting body motion when a patient is lying down includes a pad shaped to prevent the patient from rolling over the pad. The pad is shaped so that it projects outwardly 3 inches or more from the patient when attached to the patient. The base of the pad contacts the patient's skin or clothing. The pad has sidewalls which make an angle of greater than approximately 35 degrees with respect to the base. The large angle prevents the pad from acting as a ramp while the patient rolls in his or her sleep. The pad is made from a stiff foam rubber-type material or other firm synthetic or an all natural material. The pad may also be composed of a softer, but densely-packed, material. The pad may be filled with air and the firmness of the pad could be adjusted by inflating or deflating it using an inflation mechanism, as is known in the art. The pad has a removable covering which is launderable. An attachment mechanism associated with the pad and the covering attach the pad and cover to the human body. The attachment mechanism can be a hook-and-loop fastener, a sports bra type device, a series of straps, a series of snaps, a series of hooks or any other type of fastening device. In each instance, the pad can be positioned at several positions on the body, including positions along the medial plane or to the right or left of the patient's medial plane. Several pads can be attached to the patient and limit the body motion of a patient. One can be positioned on the posterior side of a patient and another can be positioned on the anterior side of a patient. In this way, the patient motion may be limited to lying on one side. Pads may also be positioned in other arrangements so as to limit the body motion of the patient.

Advantageously, the pads limit the motion of a patient while at rest or while sleeping. The pad is of such a size and shape as to prevent patients from reaching the supine position to prevent snoring or sleep apnea. In addition, the pads can be used to force a person to sleep on one part of the body in order to isolate certain areas of the body after surgery. The pads are easily understood and easily used by the patient. A patient can quickly learn to use the pads after a brief review of instructional materials, such as an audio tape, videotape, a written manual, a CD, or other computerized instruction.

DESCRIPTION OF THE PREFERRED EMBODIMENTS

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1:
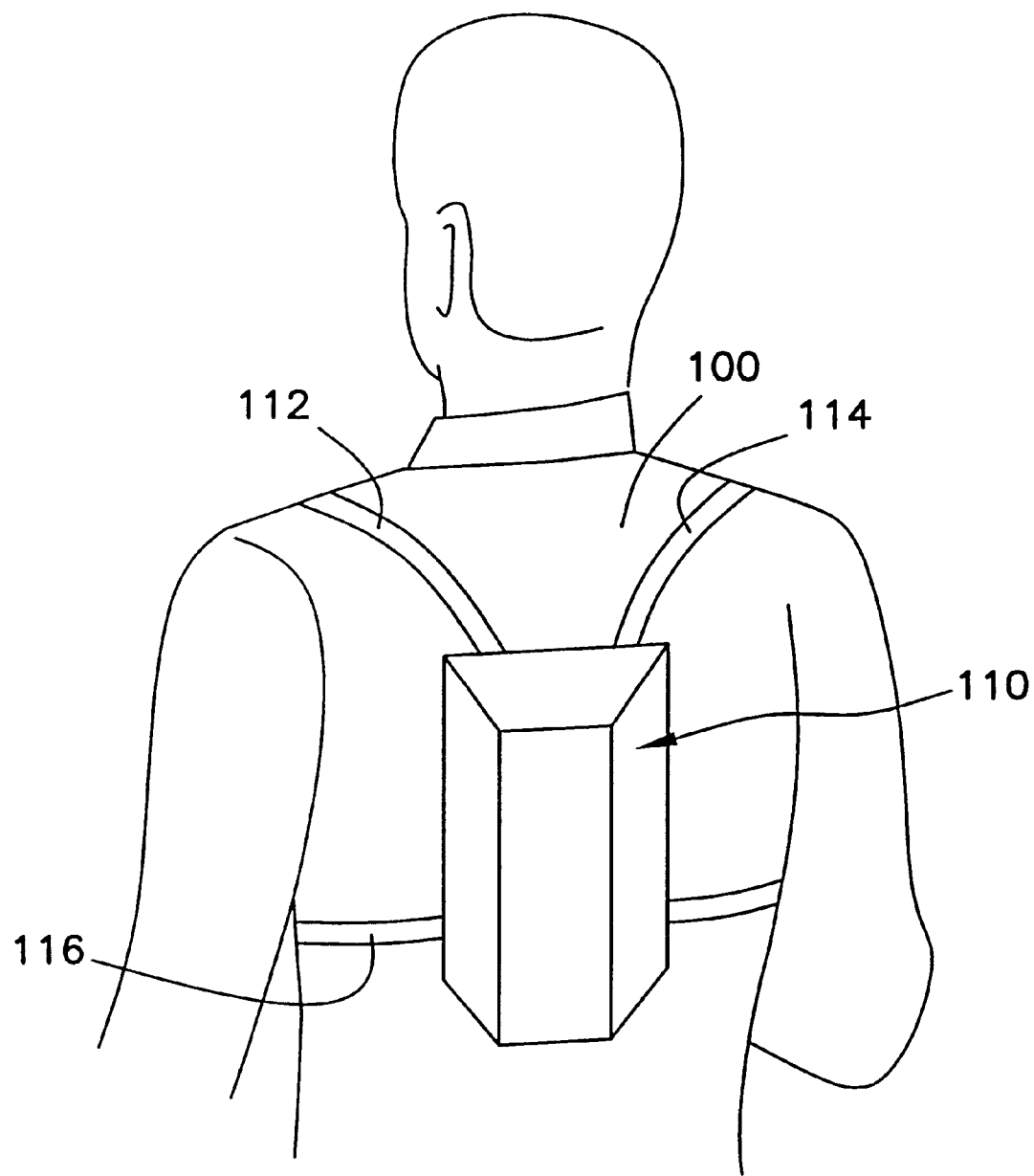
FIG. 1 is an isometric view of a pad attached to a human.

Referring to FIG. 1, FIG. 1 is an isometric view of a pad 110 attached to a patient 100. The pad 110 includes a first shoulder strap 112 and a second shoulder strap 114 as well as a third strap 116 for extending around the torso of the patient 100. The straps 112, 114 and 116 can be adjusted to hold the pad 110 in any position with respect to the back. As shown in FIG. 1, the pad 110 is strapped to the center of the back or along the medial plane of the patient 100. However, the pad 110 can be held to the right or left of the medial plane or the right or left of the center of the patient's 100 back. It should also be noted that the pad 110 projects out from the surface of the patient 100. The pad 110 is shaped so that it projects out an adequate distance so that a patient 100 will not roll over the pad 110. FIG. 1 shows the patient 100 standing after a single pad 110 has been attached to the body with straps 112, 114 and 116.

Figure 2:
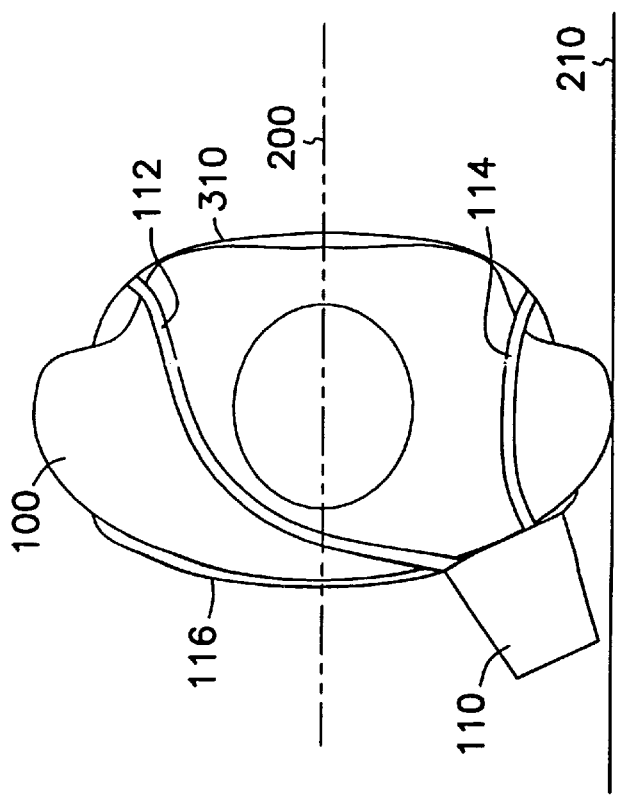
FIG. 2 is a top cross-sectional view of a human having a single pad attached thereto.

FIG. 2 is a top cross-sectional view of a human having a single pad 110 attached to the body of the patient 100. FIG. 2 shows the medial plane as line 200. Also in FIG. 2, the patient 100 is lying on a surface 210, such as a bed mattress or the like. The pad 110 is attached to the body of the patient 100 using the first strap 112, the second strap 114 and a third strap 116. The pad 110 is trapezoidally shaped in cross section and projects out from the body a sufficient distance so that the pad cannot be easily rolled over or rolled over at all. Thus, as the patient is sleeping or lying on his side, he is maintained in this position since the pad 110 will not let the patient 100 roll in a counterclockwise fashion to a supine position. It should be noted that the pad 110 may be attached so that the trapezoidal cross section is bisected by the medial plane 200 as in FIG. 1. When attached in this fashion, it would prevent a patient 100 from rolling onto their back. When attached as shown in FIG. 2, the person or patient 100 could roll in a clockwise direction and move over the torso and onto the back without having to roll over the pad 110.

Figure 3:
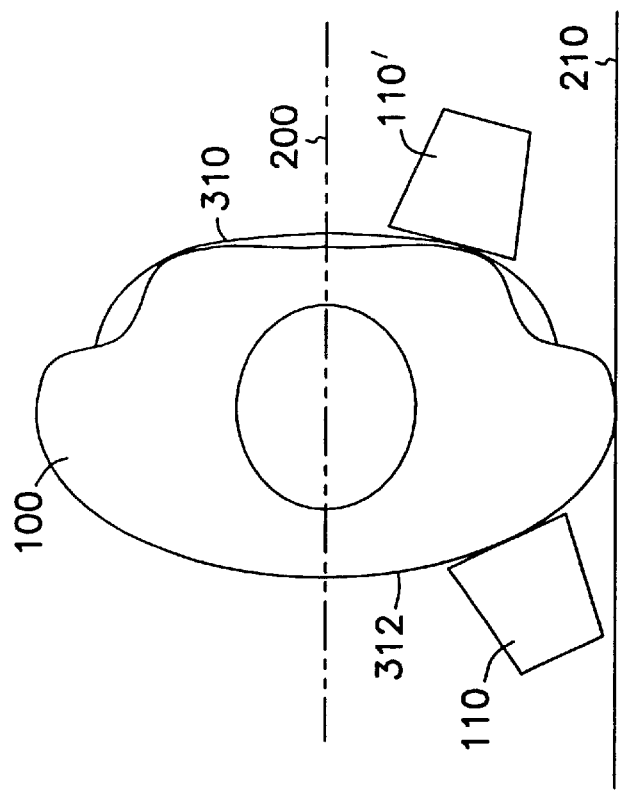
FIG. 3 is a top cross-sectional view of a human having a plurality of pads attached thereto.

FIG. 3 is a cross-sectional top view of a patient having a plurality of pads 110 and 110' attached to the surface of the patient. One pad 110' is attached to the anterior surface 310 or front of the patient 100. The other pad 110 is attached to the posterior surface 312 of the patient 100. The pads 110 and 110' are attached to the body by other than straps. The pads 110 and 110' can be attached by any number of methods. Typically, the patient 100 wears an article of clothing or sleepwear which has a series of snaps, hooks, zippers, pockets or even a portion of a hook-and-loop fastener. The pads 110 and 110' include mating hooks, snaps or hook-and-loop fasteners. The pads 110 and 110' can then be attached at a plurality of positions on the surface of the patient 100. The pads are therefore adjustable and can be positioned as desired to force or keep the patient 100 sleeping on a particular side or surface of his body. The pads 110 and 110' can then be used to isolate a portion of the body which should not be slept upon or laid on during rest or slumber. The pads 110 and 110' are attached to the patient so that the patient 100 is forced to sleep on a surface that is essentially opposite the surface to be isolated. For example, as shown in FIG. 3, the pads 110 and 110' are attached to the anterior surface 310 and the posterior surface 312 of the patient and also to the right of the medial plane 200 which passes through the patient. Therefore, the patient 100 will sleep or maintain a resting position on the right side of his or her body. As a result, any surgery that has occurred on the left side of the body is isolated and will not be slept upon. In addition, there is no chance for the patient 100 to roll past a pad since two pads 110 and 110' are attached to the body of the patient 100. Due to the fact that the pads are attachable at multiple spots on the body of the patient 100, different portions of the body can be isolated.

Figure 5:
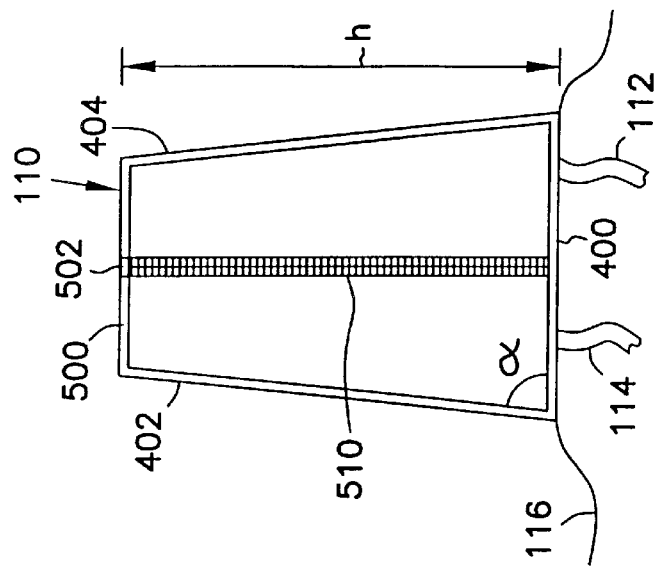
FIG. 5 is a cross-sectional view of a first preferred embodiment of a pad along line 5—5 in FIG. 4.
Figure 4:
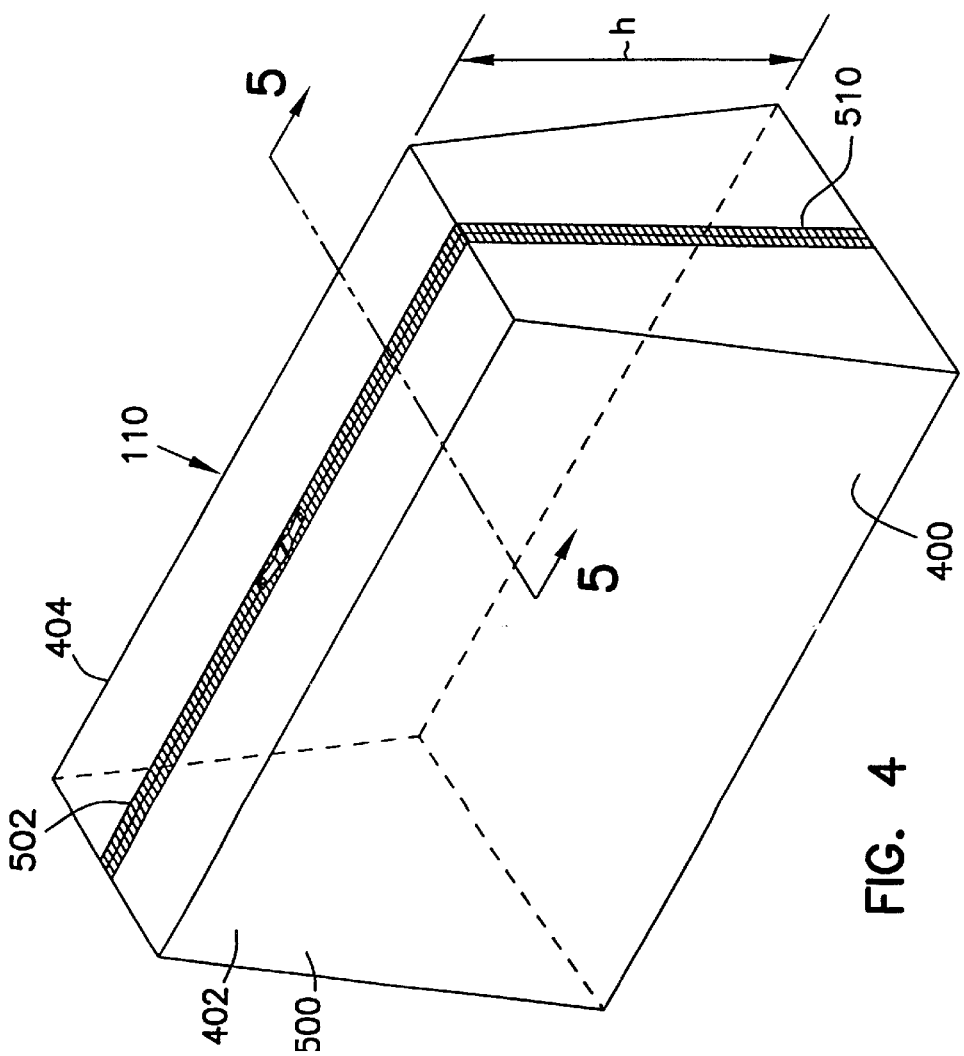
FIG. 4 is a perspective view of a first preferred embodiment of a pad.

Now turning to FIGS. 4 and 5, the shape of the pad 110 will be discussed in more detail. FIG. 4 shows an isometric view of a first preferred embodiment of the pad 110. FIG. 5 shows a cross-sectional view of the pad 110. The pad 110 has a base 400 which has a length and width. The base 400 is the portion of the pad 110 which contacts the surface of the patient 100. The pad 110 is essentially trapezoidal in cross-sectional shape. The height of the trapezoid is the height to which the pad 110 projects from the patient. It is essential that the height be at least 3 inches so that a patient cannot merely roll over the pad 110. Also essential or critical is the angle between the sidewalls 402 and 404 of the trapezoid and the base 400. The angle between sidewall 402 and the base 400 is depicted as the angle $\alpha$ in FIG. 5. The angle $\alpha$ must be more than approximately 35°, but less than 110°. Preferably, the angle $\alpha$ will be within the range of 45° to 90°. If the angle a is too small, then the sidewall 402 or 404 of the pad 110 acts as a ramp and allows the patient to roll himself or herself up or onto the ramp and past the pad 110. The pad 110 also includes a covering 500. The covering 500 is a launderable cloth. The covering 500 includes a zipper 510 which is beneath a flap 502 of the covering. In FIG. 4, the flap is shown partially broken away or removed so that the zipper 510 may be seen. Placing a flap 502 over the zipper 510 prevents the zipper 510 from snagging on a surface 210 on which the patient is resting. Advantageously, the covering 500 can be removed by unzipping the zipper and pulling the pad 110 from within its covering 500. The covering may then be washed or laundered. In FIG. 4, the pad 110 is shown without straps and in FIG. 5, the pad 110 is shown with straps 112, 114 and 116. It should be noted that the pad 110 can be made from any type of synthetic material such as foam rubber or any type of natural materials. It could also be an air-filled bladder. The cloth covering 500 can be made of a durable soft natural or synthetic fabric.

Figure 7:
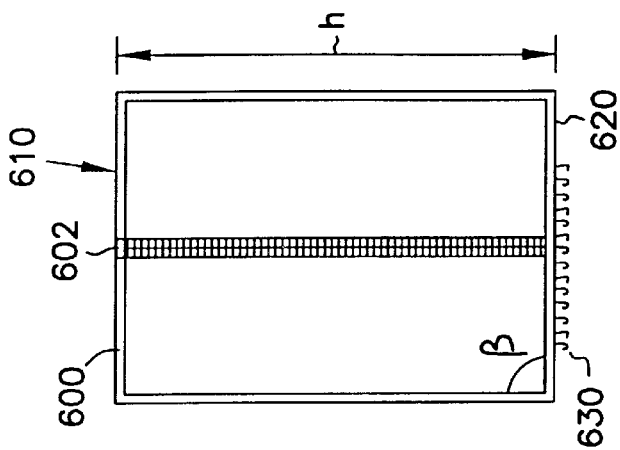
FIG. 7 is a cross-sectional view of a second preferred embodiment of a pad along line 7—7 in FIG. 6.
Figure 6:
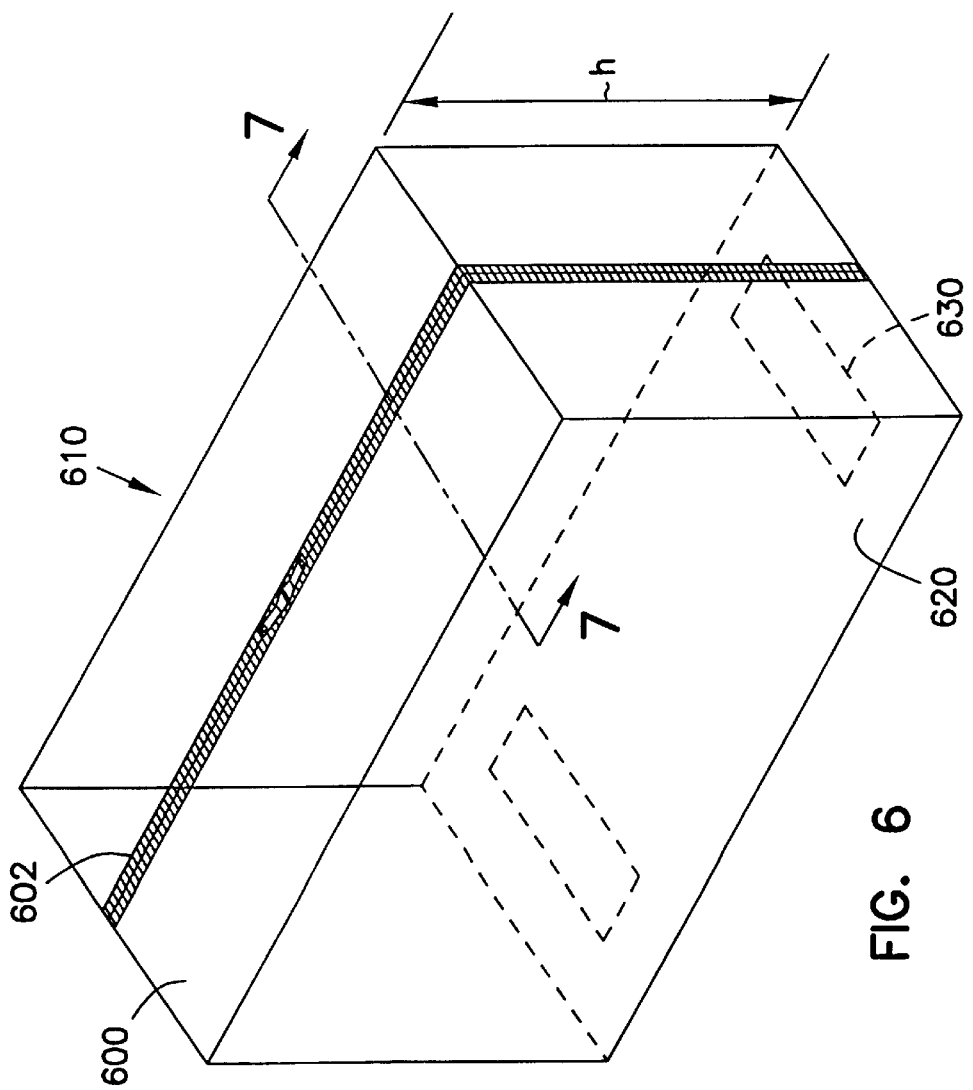
FIG. 6 is a perspective view of a second preferred embodiment of a pad.

Now turning to FIGS. 6 and 7, a second embodiment of the pad 610 will be discussed. FIG. 6 shows a perspective or isometric view of the second preferred embodiment of the pad 610 and FIG. 7 shows a cross-sectional view of the pad 610. In cross section, the pad 610 is rectangular in shape. The pad 610 has a height of at least 3 inches. The height of the pad determines the distance to which it will project from the surface of the patient 100. The pad 610 has a base 620 having a length and a width. The base 620 is the portion of the pad that contacts the patient 100. The pad 610 includes a covering 600. The covering 600 includes a zipper 602. By unzipping the zipper 602, the inside of the pad 610 can be removed and the covering 600 can be laundered. The inside of the pad 610 can be made of any natural or organic type of material such as dense or packed cotton or wheat husks or a synthetic material such as foam rubber. It could also be an air-filled bladder. The cloth covering 600 can be made of any material, but preferably is made from a soft comfortable material for the comfort of the patient 100. Attached to the bottom of the base 620 is a series of hooks from a hook-and-loop fastener. The hooks are a portion of a hook-and-loop fastener, such as commonly known by the brand name Velcro. The hooks generally can come in strips which can be sewn to the base 620. The strips of hooks are referred to by reference numeral 630 in FIGS. 6 and 7. The angle between the base 620 and one of the sidewalls of the pad 610 is depicted as $\beta$ As shown in FIGS. 6 and 7, the angle $\beta$ is essentially equal to 90°. The angle of 90° is one which will not allow the sidewalls to act as a ramp. It should be noted that pads having a triangular shape with a relatively shallow angle would be less likely to prevent a person from rolling into the supine position, since they would allow the patient to roll over or onto the pad. Essentially, if the angle $\alpha$ or $\beta$ is too shallow or too small, the pad no longer acts as a stop for the rolling motion of the patient 100 but rather acts as a ramp and allows the patient to roll over the pad. It should be noted that the pad 610 need not have a hook-and-loop fastener such as depicted by the reference numeral 630. The pad also may have snaps or hooks. In short, any method of attaching the pad to the surface of the patient so that it remains fastened when the patient tries to roll past the pad will suffice. Generally, if straps are not used, an article of clothing must be either provided with a pocket or a series of pockets or with a mating connecting device, such as the loops from a hook-and-loop fastener, receivers of the snaps attached to one of the pads or rings for fastening the hooks on a pad to the garment being worn by the patient. The article of clothing will be provided with a plurality of fasteners such that a pad 110 or 610 or any other shaped pad can be attached at multiple sites on the article of clothing.

Figure 11:
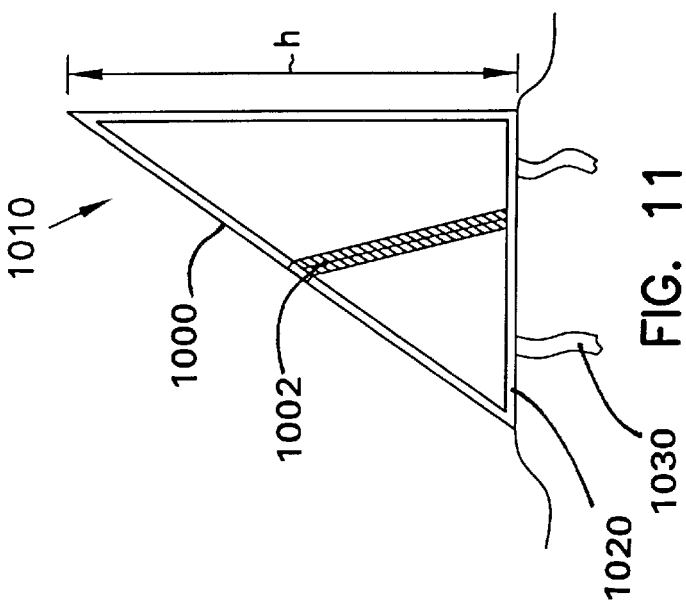
FIG. 11 is a cross-sectional view of a third preferred embodiment adding line 1-11 in FIG. 10.
Figure 10:
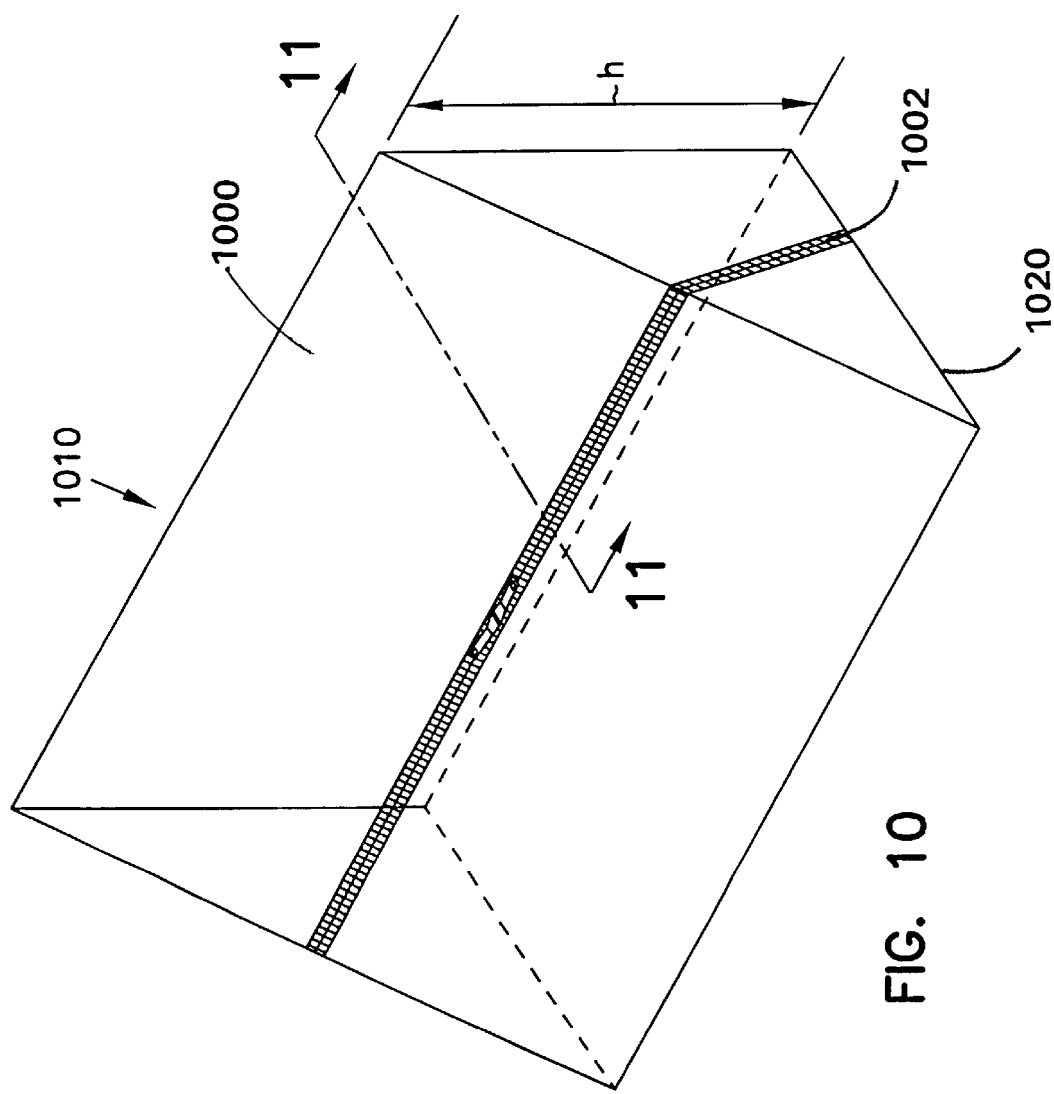
FIG. 10 is a perspective view of a third preferred embodiment of a pad.

Now turning to FIGS. 10 and 11, a third embodiment of the pad 1010 will be discussed. FIG. 10 shows a perspective or isometric view of the third preferred embodiment of the pad 1010 and FIG. 11 shows a cross-sectional view of the pad 1010. In cross section, the pad 1010 is triangular in shape. The pad 1010 has a height of at least 3 inches. The height of the pad determines the distance to which it will project from the surface of the patient 100. The pad 1010 has a base 1020 having a length and a width. The base 1020 is the portion of the pad that contacts the patient 100. The pad 1010 includes a covering 1000. The covering 1000 includes a zipper 1002. by unzipping the zipper 1002, the inside of the pad 1010 can be removed and the covering 1000 can be laundered. The inside of the pad 1010 can be made of any natural or organic type of material such as dense or packed cotton or wheat husk or a synthetic material such as foam rubber. It can also be an air-filled bladder. The covering 1000 can be made of any material, but preferably is made from a soft comfortable material for the comfort of the patient 100. Attached to the bottom of the base 1020 is a series of hooks from a hook-and-loop fastener. The hooks are a portion of a hook-and-loop fastener, such as commonly known by the brand name Velcro. The hooks generally can come in strips which can be sewn to the base 1020. The strips of hooks are referred to by reference numeral 1030, in FIGS. 10 and 11. The angle between the base 1020 and one of the angled sidewalls of the pad 1010 is depicted as γ. As shown in FIGS. 10 and 11, the angle γ is essentially equal to at least 35°. It should be noted that pads having a triangular shape with a lesser angle would be less likely to prevent a person from rolling into the supine position since they could allow the patient to roll over the pad. It should be noted that the pad 1010 need not have a hook-and-loop fastener such as depicted by the reference numeral 1030. The pad also may have snaps or hooks. In short, any method of attaching the pad to the surface of the patient so that it remains fastened when the patient tries to roll past the pad will suffice. Generally, if straps are not used, an article of clothing must be either provided with a pocket or a series of pockets or with a mating connecting device, such as the loops from a hook-and-loop fastener, receivers of the snaps attached to one of the pads or rings for fastening the hooks on a pad to the garment being worn by the patient. The article of clothing will be provided with a plurality of fasteners such that the pad 1010 can be attached at multiple sites on the article of clothing.

It should be noted that the pads may be of any shape and dimension that prevent the patient 100 from rolling over the pad into the supine position. The shapes of the pads 110, 610 and 1010 are examples of such pads. The shapes of pads 110, 610 and 1010 are not the only shapes that will serve this purpose.

Figure 8:
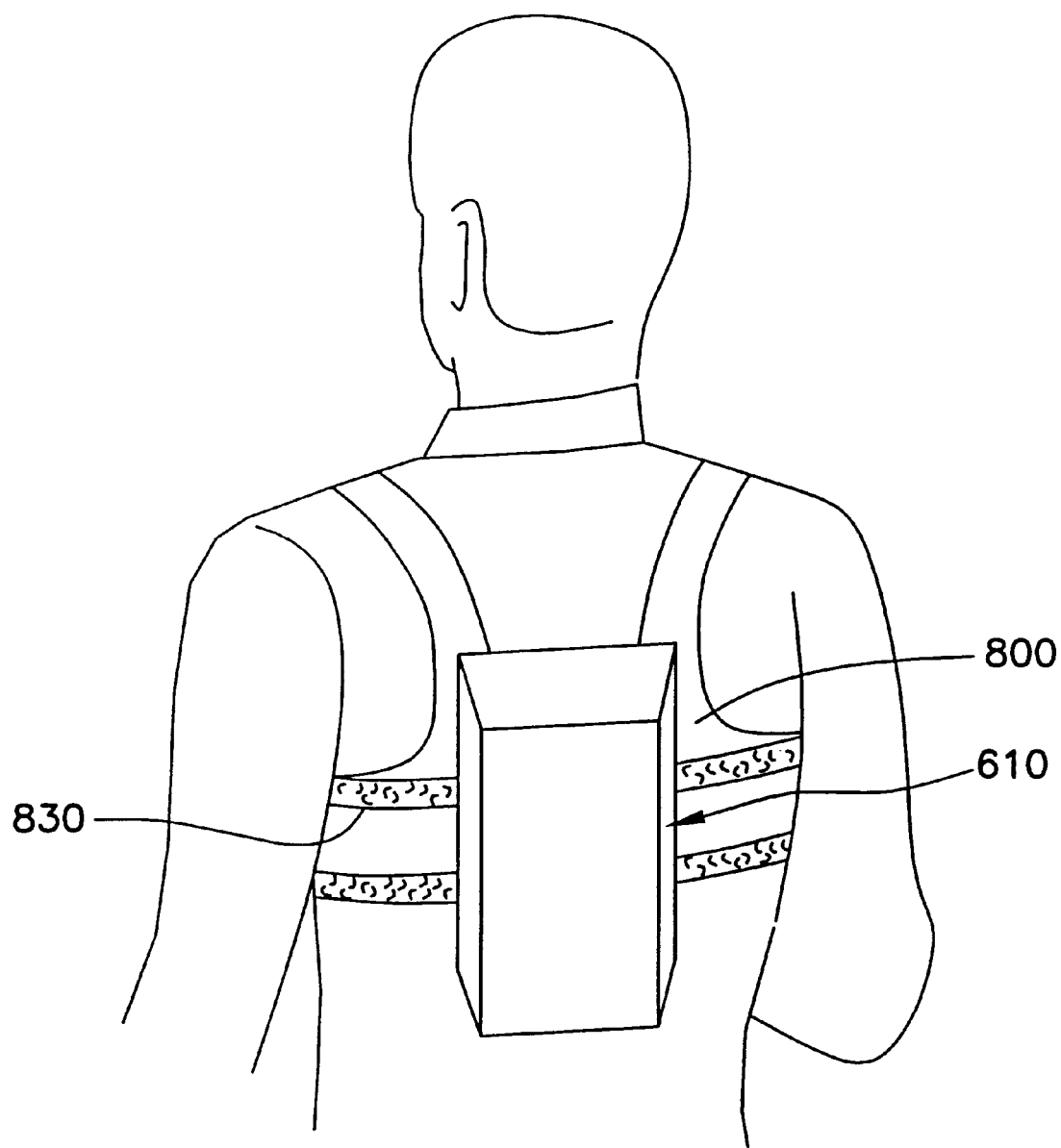
FIG. 8 is a pad attached to a sport bra type device.

FIG. 8 shows a patient 100 with a sport bra-type garment 800. The sport bra 800 has multiple sites at which a pad, such as 110 or 610, can be attached thereto. In addition, more than one pad can be attached to the patient 100 by attaching the pad 110 or 610 to one of many sites on the sport bra. The sport bra or tank top can be provided with a plurality of strips of mating fasteners, such as loop fasteners from a hook-and-loop fastening means commonly available and known as Velcro. In addition, hooks or snaps or other similar fasteners may be used. As a result, one or more of the pads 110 or 610 can be attached to the sport bra or tank top 800. Advantageously, a sport bra or abbreviated tank top 800 like the pad with straps, allows the patient to sleep without pajamas if so desired. In addition, since there are multiple sites on the article of clothing 800, the pads can be placed at a variety of positions with respect to the body to thereby isolate other body portions which should not undergo the forces associated with lying on these body parts during rest or slumber.

Figure 9:
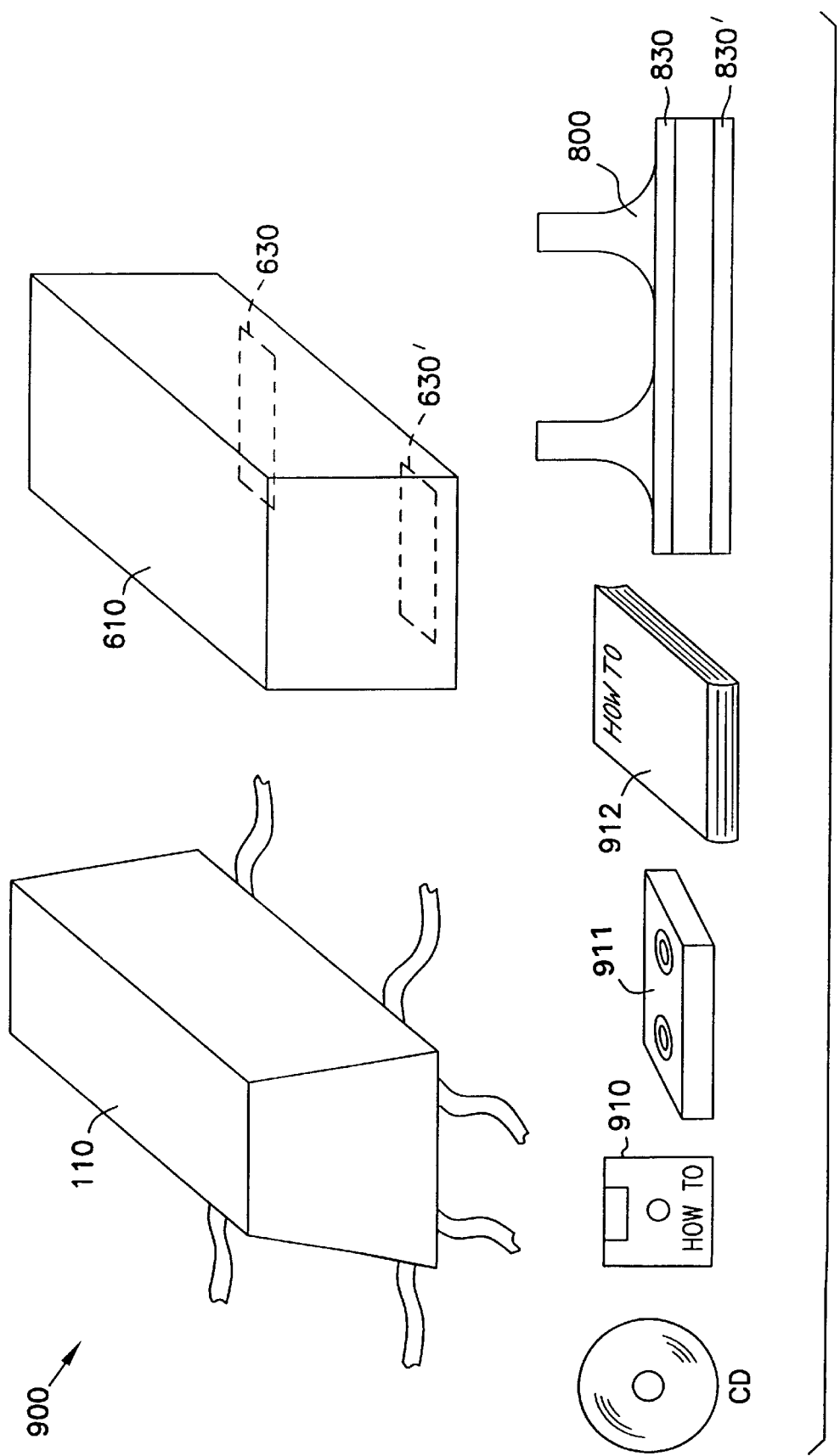
FIG. 9 is a view of a kit including a pad and instructional material regarding use of the pad.

FIG. 9 shows the content or probable contents of a kit 900 which could be given to a patient 100. At the minimum, the kit includes a pad 110 which can be attached to the surface of the patient 100 as well as some instructional material, such as a videotape 910 or an instruction manual 912, CD or computer program. Instructional materials will tell the patient how to use the pad 110. If two pads are required, either a second kit can be purchased or the kit can include a second pad, such as the pad 610 shown in FIG. 9. The instructional video 910 or instruction manual and 912, CD 911 or computer program 913 respectively can also cover the method of use for having two pads. In addition, the kit 900 may include an article of clothing such as the sport bra-type garment or abbreviated tank top 800. The article of clothing may have a strip of a hook-and-loop fastener, hooks or snaps such as 830 and 830' attached to the article of clothing 800. These two strips, hooks or snaps would be positioned so that they would mate or attach to corresponding strips, hooks or snaps 630 and 630' on a pad such as 610. This would provide for fully adjustable positioning of the pad 610 on the body of the patient and on the article of clothing 800.

The method of use is fairly straightforward. The portion of the body which is to be isolated is first determined. Once it has been determined what portion of the body is to be isolated, the first pad is applied or attached to a surface of the patient 100. A second pad can also be applied to the surface of the body of the patient. The first pad and second pad are positioned so that movement during sleep, lying down or rest, will be limited to a certain portion of the body. The certain portion of the body which will be in contact with the resting surface 210 will not be the portion of the body which is to be isolated, such as a hip or knee that has recently undergone surgery or an incision from any other surgery.

Advantageously, the pads limit the motion of a patient while at rest or while sleeping. The pad is of such a size and shape to prevent patients from reaching the supine position to prevent snoring or sleep apnea. In addition, the pads can be used to force a person to sleep on one part of the body and isolate certain areas on the body after surgery. The pads are easily understood and easily used by the patient. A patient can quickly learn to use the pads after a brief review of instructional materials, such as an audio tape, videotape, CD, computer program or a manual.

The use of a pad or pads would provide the patient with an after-surgery solution that would allow them to be released from the hospital sooner. A quick release from the hospital is best for the patient's mental well-being and is also desirable from the standpoint of insurance providers.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A snoring prevention apparatus comprising:

an exterior cover;

a first over the shoulder strap attached to the exterior cover;

a second over the shoulder strap attached to the exterior cover;

a third waist strap attached to the exterior cover of sufficient length to pass around the patient at approximately the waist attached to the exterior cover; and an inflatable air bladder contained within the exterior cover, the air bladder and exterior cover forming a pad, the pad having a base and first and second sidewalls extending from the base, the air bladder including a mechanism so that the firmness of the air bladder may be adjusted by inflating or deflating the air bladder, the first, second, and third straps being configured to attach to a patient's body such that the base of the pad is affixed to the patient's back at a location which prevents the patient from lying on the patient's back, the first sidewall of the pad being angled with respect to the base in the direction of the second sidewall at an angle in the range between approximately 35° and less than 110°, the exterior cover and air bladder having a height of at least three inches and sized such that the pad extends from the patient's body at least three inches when the base of the pad is affixed to the patient's back during use.

2. The apparatus of claim 1 wherein the first shoulder strap is adjustable, and the second shoulder strap is adjustable, and the third waist strap is adjustable.

3. The apparatus of claim 1 wherein the exterior cover includes a portion of a hook and loop fastener.

4. The apparatus of claim 1 wherein the pad has a substantially trapezoidal cross section.

* * * * *